United States Patent [19]

Harnden et al.

[11] Patent Number: 5,246,937

[45] Date of Patent: Sep. 21, 1993

[54] PURINE DERIVATIVES

[75] Inventors: Michael R. Harnden, Horsham; Richard L. Jarvest, Surbiton, both of England

[73] Assignee: Beecham Group p.l.c., England

[21] Appl. No.: 824,131

[22] Filed: Jan. 22, 1992

Related U.S. Application Data

[60] Division of Ser. No. 285,399, Dec. 6, 1991, abandoned, which is a continuation-in-part of Ser. No. 777,188, Sep. 18, 1985, abandoned.

[51] Int. Cl.⁵ .................... C07D 473/26; A61K 31/52
[52] U.S. Cl. .................... 514/261; 544/276; 544/277
[58] Field of Search .............. 544/276, 277; 514/261

[56] References Cited

U.S. PATENT DOCUMENTS 5,036,071  7/1991  Johannson .................... 544/276

Primary Examiner—Nicholas S. Rizzo
Attorney, Agent, or Firm—Yuriy P. Stercho; Stuart R. Suter; Edward T. Lentz

[57] ABSTRACT

The present invention provides antiviral compounds of Formula (I):

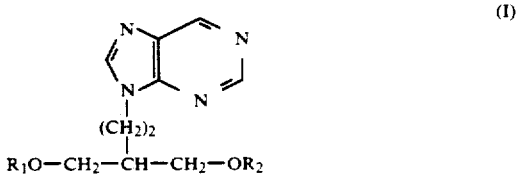

(I)

pharmaceutical compositions prepared therefrom, and methods of treatment of viral infections therewith.

19 Claims, No Drawings

PURINE DERIVATIVES

This is a Divisional of application Ser. No. 07/285,399 filed Dec. 6, 1991 now abandoned which is a continuation-in-part of Ser. No. 777,188 filed Sep. 18, 1985, now abandoned.

The present invention relates to compounds having antiviral activity, processes for their preparation and pharmaceutical compositions containing them.

The compound 9-(4-hydroxy-3-hydroxymethylbut-1-yl) guanine of formula (A)

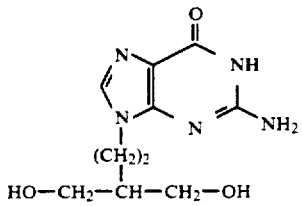

is disclosed in Synthetic Communications, 2(6), 345–351 (1972) but no pharmaceutical activity has been indicated for the compound in this document. We have subsequently shown that the compound of formula (A) does have pharmaceutical activity, and this is disclosed in our Published European Pat. Appn. 0141 927.

We have now prepared a series of analogues of the compound of formula (A) which has useful oral absorption properties and is converted in vivo to the compound of formula (A) which has anti-viral activity.

According to the present invention there is provided a compound of formula (I)

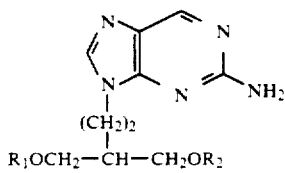

or a salt thereof, wherein $R_1$ and $R_2$ are each independently hydrogen, acyl or phosphate, provided that when one of $R_1$ or $R_2$ is phosphate, the other is hydrogen; or $R_1$ and $R_2$ are joined together to form a cyclic acetal group, a cyclic carbonate group or a cyclic phosphate group.

Examples of acyl groups for $R_1$ and $R_2$ are those where the group $R_1O$— or $R_2O$— is a pharmaceutically acceptable ester group, such as a carboxylic ester group.

Suitable acyl groups for $R_1$ and $R_2$ are

where $R_3$ is $C_{1-6}$ alkyl, $C_{1-6}$ alkoxy, or optionally substituted aryl.

As used herein the term 'aryl' includes phenyl which may be optionally substituted with one or two groups selected from $C_{1-6}$ alkyl, $C_{1-6}$ alkoxy or halo such as fluoro or chloro.

Preferably $R_3$ is methyl, ethyl, propyl, methoxy, or phenyl.

Suitably when $R_1$ and $R_2$ are joined together, they constitute a group

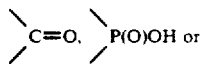

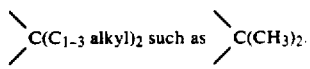

A suitable example of a compound of formula (I) is the compound where one of $R_1$ or $R_2$ is

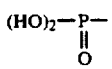

and the other is hydrogen.

In the case of compounds of formula (I) wherein one of $R_1$ or $R_2$ is an acyl or phosphate group, the compound exists in two enantiomeric forms. The invention includes both enantiomers in isolated form and mixtures thereof.

The compounds of the invention may be in crystalline form or as hydrates and it is intended that both forms are encompassed by the expression 'compound of formula (I)' used herein.

Salts of the compound of formula (I) are preferably pharmaceutically acceptable, but non-pharmaceutically acceptable salts are also within the scope of the present invention, since these are useful as intermediates in the preparation of pharmaceutically acceptable compounds.

Examples of pharmaceutically acceptable salts of the compound of formula (I) are acid addition salts formed with a pharmaceutically acceptable acid such as hydrochloric acid, orthophosphoric acid and sulphuric acid.

When the compound of formula (I) contains a phosphate group suitable salts include metal salts, such as aluminum, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine.

Suitable compounds of formula (I) include;
2-amino-9-(4-hydroxy-3-hydroxymethylbut-1-yl)purine;
2-amino-9-(4-acetoxy-3-acetoxymethylbut-1-yl)purine;
2-amino-9-(4-acetoxy-3-hydroxymethylbut-1-yl)purine;
2-amino-9-(3-hydroxymethyl-4-methoxycarbonyloxybut-1-yl)purine;
2-amino-9-[2-(2,2-dimethyl-1,3-dioxan-5-yl)ethyl]purine;
2-amino-9-(4-propionyloxy-3-propionyloxymethylbut-1-yl)purine;
2-amino-9-(4-butyryloxy-3-hydroxymethylbut-1-yl)purine;
2-amino-9-(4-benzoyloxy-3-hydroxymethylbut-1-yl)purine;
2-amino-9-(4-hydroxy-3-hydroxymethylbut-1-yl)purine 4'-phosphate;
2-amino-9-(4-hydroxy-3-hydroxymethylbut-1-yl)purine 4':4''phosphate;

and pharmaceutically aceptable salts thereof.

The compounds of the present invention are potentially useful in the treatment of infections caused by herpes viruses, such as herpes simplex type 1, herpes simplex type 2 and varicella zoster viruses.

Accordingly, the present invention also provides a compound of formula (I) or a pharmaceutically acceptable salt thereof, for use as an active therapeutic substance and in particular for use in the treatment of viral infections.

The compound of formula (I) wherein $R_1$ and $R_2$ are both hydrogen or a salt thereof may be prepared by hydrolysing the 1,3-dioxane ring of a compound of formula (II)

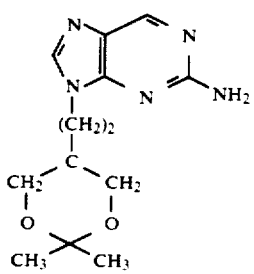
(II)

and subsequently, if necessary, converting the compound of formula (I) thus formed to the free base or to a different salt thereof.

Preferably the hydrolysis of the compound of formula (II) is carried out in acid medium, conveniently aqueous hydrochloric acid.

The compound of formula (II) is itself an example of a compound of formula (I) and may be prepared by reducing a compound of formula (III)

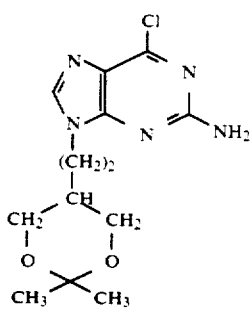
(III)

The reduction is preferably carried out catalytically, using palladium-on-charcoal, and the subsequent hydrolysis to the compound of formula (I) may be conveniently performed directly on the reaction product mixture.

The intermediate compound of formula (III) may be prepared by treating a compound of formula (IV)

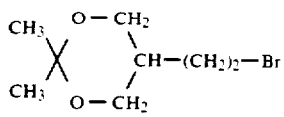
(IV)

with a compound of formula (V)

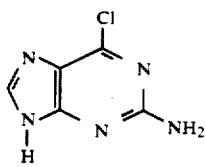
(V)

The reaction may be carried out in an inert organic solvent, preferably dimethylformamide, in the presence of an inorganic base, preferably potassium carbonate.

The compound of formula (IV) may itself be prepared by brominating a compound of formula (VI)

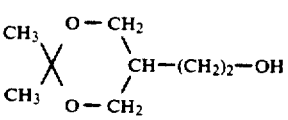
(VI)

The reaction is preferably carried out by treating the compound of formula (VI) with carbon tetrabromide and triphenylphosphine in an organic, aprotic solvent such as dimethylformamide.

The compound of formula (VI) may itself be prepared by treating a compound of formula (VII)

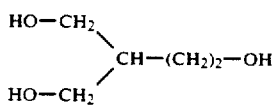
(VII)

with 2,2-dimethoxypropane and p-toluenesulphonic acid in the presence of acetone or tetrahydrofuran.

Compounds of formula (I) werein $R_1$ and $R_2$ are acyl groups or are joined together to form a cyclic carbonate group can be prepared by reduction of a compound of formula (VIII)

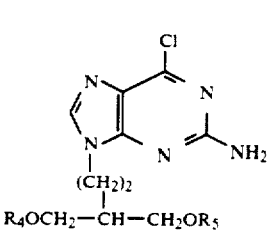
(VIII)

wherein $R_4$ and $R_5$ are the same or different acyl groups, or $R_4$ and $R_5$ are joined together to form a cyclic carbonate group.

Suitable acyl groups for $R_4$ and $R_5$ include groups

as hereinbefore defined.

The reduction is suitably carried out under conditions described above for the reduction of a compound of formula (III).

Compounds of formula (I) wherein $R_1$ and $R_2$ are acyl groups can be converted to a compound of formula (I) wherein $R_1$ and or $R_2$ are hydrogen by conventional deacylation or partial deacylation processes. For example, reaction with methanolic ammonia can be used to effect complete deacylation to yield compound of formula (I) wherein both $R_1$ and $R_2$ are hydrogen. Reaction with a mild base such as potassium carbonate can result in partial deacylation to produce a compound of formula (I) wherein one of $R_1$ or $R_2$ is hydrogen and the other is an acyl group.

Compounds of formula (VIII), may be prepared by treating the compound of formula (V) as hereinbefore defined, with a compound of formula (X)

in which $R_4$ and $R_5$ are as defined in formula (VIII) and Z is a leaving group such as Cl, Br or I, preferably Br.

The compound of formula (V) is a known compound.

Compounds of formula (X) in which Z is bromine may be prepared by brominating a compound of formula (XI).

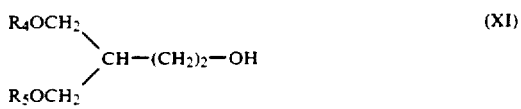

preferably by treatment with carbon tetrabromide and triphenylphosphine in an organic, aprotic solvent, such as dimethylformamide.

Compounds of formula (X) in which Z is Cl or I may be prepared in an analogous manner.

Compounds of formula (XI) in which $R_4$ and $R_5$ are the same and are acyl groups may be prepared according to the following schematic process:

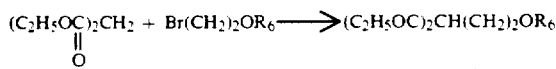

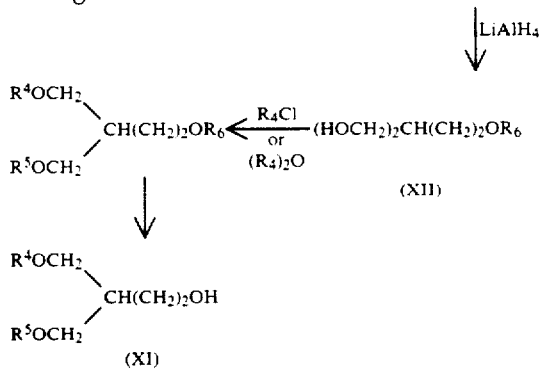

wherein $R^6$ is a removable protecting group.

Suitably $R_6$ is a group removable by hydrolysis or hydrogenolysis.

Preferably $R_6$ is a group removable by hydrogenolysis such as benzyl. This group can be removed by conventional methods for example by using hydrogen in the presence of a palladium/carbon catalyst.

Compounds of formula (XI) wherein $R_4$ and $R_5$ are joined together to form a cyclic carbonate group may be prepared by reaction of a compound formula (XII)

wherein $R_6$ is a hereinbefore defined with phosgene or 1,1'-carbonyldiimidazole, and thereafter if desired removing the protecting group $R_6$. The reaction is suitably carried out in a dry organic solvent such as pyridine at a temperature of from 0°-50° C., conveniently at ambient temperature.

The above described processes for preparing the compound of formula (III) and compounds of formula (VIII) are also disclosed in Published European European Patent Application No. 0141 927.

Compounds of formula (I) wherein $R_1$ and/or $R_2$ is acyl may be prepared by esterifying a compound of formula (I) wherein $R_1$ and $R_2$ is hydrogen by conventional methods. If necessary during the esterification process the —$NH_2$ group and optionally also one of the —$OR_1$, or —$OR_2$ groups may be protected by a suitable protecting group such as trityl or monomethoxytrityl. The product is subsequently deprotected for example by treatment with acid such as acetic acid. For example, compounds of formula (I) wherein $R_1O$— and/or $R_2O$— is a carboxylic ester group may be prepared by reaction of a compound of formula (I) which has been optionally protected as described above with (a), an appropriate carboxylic acid chloride or (b) an appropriate carboxylic acid anhydride or (c) an appropriate carboxylic acid in the presence of a dehydrating agent such as dicyclohexylcarbodiimide (DCCI).

Compounds of formula (I) wherein $R_1$ and $R_2$ form a cyclic carbonate group can be prepared by reaction of a compound of formula (I) wherein $R_1$ and $R_2$ are hydrogen and the $NH_2$ group is optionally protected; with phosgene or 1,1-carbonyldiimidazole, and thereafter if necessary deprotecting the product. Suitable protecting groups for the $NH_2$ group include trityl and monomethoxytrityl as described above. The reaction is suitably carried out in a dry organic solvent such as pyridine at a temperature of from 0°-50° C., conveniently at ambient temperature.

Compounds of formula (I) wherein one of $R_1$ or $R_2$ is phosphate or $R_1$ and $R_2$ together form a cyclic phosphate can be prepared by treating a compound formula (XIII)

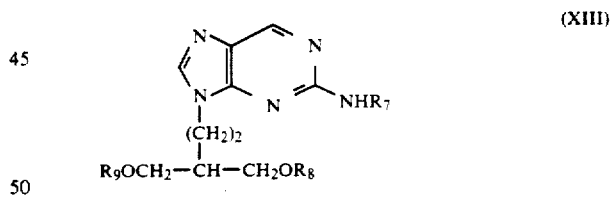

wherein $R_7$ is a protecting group and $R_8$ and $R_9$ are hydrogen or a protecting group provided that one of $R_8$ or $R_9$ is hydrogen; with a phosphorylating agent and thereafter if desired deprotecting resultant product. When $R_8$ and $R_9$ are both hydrogen, a cyclic phosphate compound is produced. Suitable protecting groups for $R_7$ and $R_8$ or $R_9$ are trityl or monomethoxytrityl. Deprotection of the resultant product can then be effected by treatment with acid such as acetic acid.

A suitable phosphorylating agent is phosphorus oxychloride, optionally in the presence of a base such as pyridine.

In addition, when one of $R_8$ or $R_9$ is a protecting group cyanoethyl phosphoric acid can be employed as a phosphorylating agent in order to produce a compound of formula (I) wherein one of $R_1$ or $R_2$ is phosphate.

The reaction product after treatment with cyanoethyl phosphoric acid is treated with aqueous ammonia, which yields the ammonium salt of the phosphate ester as the final product.

Compounds of formula (XIII) can be prepared by protection of a compound of formula (I) wherein $R_1$ and $R_2$ is hydrogen, for example by reaction with a trityl or monomethoxytrityl halide such as monomethoxytrityl chloride.

Alternatively compounds of formula (I) wherein $R_1$ and $R_2$ are joined together to form a cyclic phosphate can be prepared from a compound of formula (I) wherein one of $R_1$ or $R_2$ is phosphate and the other is hydrogen by cyclisation of the monophosphate for example using dicyclohexylcarbodiimide.

Compounds of formula (I) wherein one of $R_1$ or $R_2$ is acyl and the other is hydrogen or $R_1$ and $R_2$ together form a cyclic acetal can be prepared by reacting a compound of formula (I) wherein $R_1$ and $R_2$ are hydrogen with a compound of formula (XIV)

$$(R_{10})_mC(OR_{11})_n \qquad (XIV)$$

wherein
$R_{10}$ is $C_{1-6}$ alkyl,
$R_{11}$ is $C_{1-6}$ alkyl,
m is 0,1 or 2, and
n is an integer of 2, 3 or 4
provided that m+n is equal to 4, and thereafter, if n is 3 or 4, hydrolysing the product.

When a compound of formula (I) in which $R_1$ and $R_2$ is a cyclic acetal is required, a compound of formula (XIV) wherein m is 2 and n is 2 is employed. For example, when m is 2, n is 2 and $R_{10}$ is methyl, the product is the compound of formula (II) as hereinbefore defined. The reaction is suitably carried out in an inert organic solvent such as tetrahydrofuran or N,N-dimethylformamide, in the presence of an acid such as p-toluene sulphonic acid.

Where necessary the subsequent hydrolysis step is an aqueous hydrolysis preferably carried out in the presence of an acid such as p-toluene sulphonic acid.

Compounds of formula (XIV) are known compounds or can be prepared from known compounds by known methods.

Compounds of formula (I) or pharmaceutically acceptable salts thereof may be formulated for use in a pharmaceutical composition. Accordingly, in a further aspect of the invention, there is provided a pharmaceutical composition which comprises a compound of formula (I) or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the composition may be in the form of a cream, lotion or ointment. These formulations may be conventional formulations well known in the art, for example, as described in standard books of pharmaceutics and cosmetics, such as Harry's Cosmeticology published by Leonard Hill Books and the British Pharmacopaeia.

The composition for application to the eyes may be a conventional eye-drop composition well known in the art, or an ointment composition.

Preferably, the composition of this invention is in unit dosage form or in some other form that the patient may administer to himself a single dose. A suitable dosage unit might contain from 30 mg to 1 g of active ingredient, for example 100 to 500 mg.

Such doses may be administered 1 to 4 times a day or more usually 2 or 3 times a day. The effective dose of compound will in general be in the range of from 1.0 to 20 mg/kg of body weight per day or more usually 2.0 to 10 mg/kg per day.

No toxicological effects are indicated at the above described dosage levels.

In a further aspect of the invention there is provided a method of treating viral infections in a human or non-human animal, which comprises administering to the animal an effective, non-toxic amount of a compound of formula (I) or a pharmaceutically acceptable salt thereof.

The following examples illustrate the invention.

EXAMPLE 1

2-Amino-9-(4-hydroxy-3-hydroxymethylbut-1-yl)purine

Method A

To a solution of 2-amino-6-chloro-9-[2-(2,2-dimethyl-1,3-dioxan-5-yl)ethyl]purine (0.54 g, 1.75 mmol) in ethanol (10 ml) and cyclohexene (20 ml) was added 10% palladium-on-charcoal (400 mg) and the solution was refluxed for 7 hours. A further quantity of catalyst (200 mg) was added and the solution was refluxed overnight. The solution was filtered and washed through with methanol. To the filtrate was added hydrochloric acid (5M, 0.3 ml) and water (0.7 ml) and the solution was stirred for 30 minutes at room temperature. The solution was neutralised by addition of aqueous sodium bicarbonate and the solvent was removed. The residue was purified by column chromatography on silica gel eluting with chloroform-methanol (5:1, 4:1) to afford 2-amino-9-(4-hydroxy-3-hydroxymethylbut-1-yl)purine as a crystalline solid (150 mg, 36%), m.p. 156°–158° C.; λmax (H$_2$O) 242 and 303 nm; λmax (KBr) 3320, 3210, 1640, 1610, 1580, and 1430 cm$^{-1}$; δ$_H$ [(CD$_3$)$_2$SO] 1.47 (1H, m, 3'-H), 1.78 (2H, q, J 7.2 Hz, 2'-H), 3.3–3.5 (4H, m, 2×4'-H), 4.12 (2H, t, J 7.4 Hz, 1'-H), 4.42 (2H, t, J 5.2 Hz, D$_2$O exchangeable, 2×OH), 6.45 (2H, s, D$_2$O exchangeable, 2-NH$_2$), 8.06 (1H, s, 8-H), and 8.56 (1H, s, 6-H); (Found: C, 50.61; H, 6.45; N, 29.62%. C$_{10}$H$_{15}$N$_5$O$_2$ requires: C, 50.62; H, 6.37; N, 29.52%).

Method B (alternative reduction reaction)

To a solution of ammonium formate in methanol (400 mM, 3 ml) were added 2-amino-6-chloro-9-[2-(2,2-dimethyl-1,3-dioxan-5-yl)ethyl]purine (90 mg, 0.3 mmol) and 10% palladium-on-charcoal (28 mg) and the mixture was heated under reflux. After 1.5 hours reduction to 2-amino-9-[2-(2,2-dimethyl-1,3-dioxan-5-yl)ethyl]purine was complete.

EXAMPLE 2

9-(4-Acetoxy-3-acetomethylbut-1-yl)-2-aminopurine

A suspension of 9-(4-acetoxy-3-acetoxymethylbut-1-yl)-2-amino-6-chloropurine (0.36 g, 1.0 mmol) and 10% palladium-on-charcoal (30 mg) in methanol containing ammonium formate (400 mM, 10 ml) was heated under reflux for 30 minutes. The mixture was allowed to cool, filtered and the solvent removed. The residue was taken up in water and the solution extracted twice with chloroform. The organic layers were combined, dried (magnesium sulphate) and the solvent removed to afford 9-(4-acetoxy-3-acetoxymethylbut-1-yl)-2-aminopurine (0.29 g, 90%). Recrystallisation from ethyl acetate-hexane gave white shiny plates (0.25 g, 78%) m.p. 102°–104° C.; $\lambda$max (MeOH) 222 (27,500), 244 (4,890), and 309 (7,160) nm; $\nu$max (KBr) 3340, 3170, 1745, 1730, 1660, 1615 and 1580 cm$^{-1}$; $\delta_H$ (CDCl$_3$) 1.90–2.05 (3H, m, 2'-H and 3'-H), 2.07 (6H, s, 2×CH$_3$), 4.15 (4H, d, J 5.2 Hz, 2×4'-H), 4.21 (2H, t, J 7.2 Hz, 1'-H), 5.16 (2H, br s, 2-NH$_2$), 7.79 (1H, s, 8-H), and 8.70 (1H, s, 6-H); (Found: C, 52.10; H, 6.00; N, 21.49%. C$_{14}$H$_{19}$N$_5$O$_4$ requires C, 52.33; H, 5.96; N, 21.79%).

EXAMPLE 3

2-Amino-9-(4-hydroxy-3-hydroxymethylbut-1-yl)purine

To a suspension of 9-(4-acetoxy-3-acetoxymethylbut-1-yl)-2-amino-6-chloropurine (4.86 g, 13.7 mmol) in methanol (140 ml) containing ammonium formate (400 mM) was added 10% palladium-on-charcoal (0.4 g) and the mixture was heated under reflux for 40 minutes. After cooling the solution was filtered and the solvent removed. The residue was taken up in water and extracted with chloroform (100 ml and 50 ml). The organic layers were combined, dried (magnesium sulphate) and the solvent removed. The residue was dissolved in methanol saturated with ammonia at 0° C. (150 ml) and the solution was stirred for 20 hours. The solvent was removed and the residue suspended in chloroform (20 ml) and filtered. The solid was recrystallised from isopropanol-water and a second recrystallisation was carried out from the mother liquors from ethanol (total 2.71 g, 83%).

EXAMPLE 4

9-(4-Acetoxy-3-hydroxymethylbut-1-yl)-2-aminopurine

To a solution of 9-(4-acetoxy-3-acetoxymethylbut-1-yl)-2-aminopurine (0.48 g, 1.5 mmol) in methanol (9 ml) was added anhydrous potassium carbonate (14 mg, 0.1 mmol) and the solution was stirred for 20 minutes. Two drops of glacial acetic acid were added, the solution was filtered and the solvent was removed. The residue was purified by column chromatography on silica gel eluting with chloroform-methanol (15:1, 10:1) to afford 9-(4-acetoxy-3-hydroxymethylbut-1-yl)-2-aminopurine as a white crystalline solid (124 mg, 30%), m.p. 166°–168°; $\nu_{max}$ (KBr) 3440, 3220, 1720, 1650, 1615, and 1580 cm$^{-1}$; $\delta_H$ [(CD$_3$)$_2$SO] 1.68 (1H, m, 3'-H), 1.82 (2H, m, 2'-H), 1.98 (3H, s, CH$_3$), 3.41 (2H, t, J4.8 Hz, D$_2$O exchange gives d, CH$_2$OH), 3.9–4.05 (2H, AB part of ABX, $J_{AB}$ 10.9 Hz and $J_{AX}$=$J_{BX}$ 5.8 Hz, CH$_2$OCO), 4.12 (2H, t, J 7.2 Hz, 1'-H), 4.62 (1H, t, J 5.0 Hz, D$_2$O exchangeable, OH), 6.44 (2H, s, D$_2$O exchangeable, 2-NH$_2$), 8.07 (1H, s, 8-H), and 8.56 (1H, s, 6-H); (Observed M$^+$, 279.1326. C$_{12}$H$_{17}$N$_5$O$_3$ requires 279.1331).

EXAMPLE 5

2-Amino-9-(3-hydroxymethyl-4-methoxycarbonyloxybut-1-yl)purine

To a suspension of 2-amino-9-(4-hydroxy-3-hydroxymethylbut-1-yl)purine (237 mg, 1.0 mmol) in dry tetrahydrofuran (3 ml) were added p-toluenesulphonic acid monohydrate (0.21 g, 1.1 mmol) and tetramethyl orthocarbonate (0.53 ml, 4.0 mmol) and the mixture was stirred for 100 minutes. Water (0.8 ml) was added and after a further 15 minutes the solution was neutralised by addition of aqueous sodium bicarbonate. The solvent was removed and the residue was extracted with chloroform-methanol (3:1). The solvent was removed and the residue was purified by column chromatography on silica gel eluting with chloroform-methanol (10:1) to afford 2-amino-9-(3-hydroxymethyl-4-methoxycarbonyloxybut-1-yl) purine which was obtained as a white crystalline solid after trituration with ethyl acetate (65 mg, 22%), m.p. 129°–132°; $\nu_{max}$ (KBr) 3440, 3220, 1745, 1650, 1615, and 1580 cm$^{-1}$; $\delta_H$ [(CD$_3$)$_2$SO] 1.73 (1H, m, 3'-H), 1.81 (2H, m, 2'-H), 3.41 (2H, t, 5.1 Hz, D$_2$O exchange gives d, CH$_2$OH) 3.68 (3H, s, CH$_3$), 4.0–4.2 (4H, m, CH$_2$OCO and 1'-H), 4.65 (1H, t, J 5.2 Hz, D$_2$O exchangeable, OH), 6.44 (2H, s, D$_2$O exchangeable, 2-NH$_2$), 8.06 (1H, s, 8-H), and 8.55 (1H, s, 6-H); (Observed M$^+$, 295.1286, C$_{12}$H$_{17}$N$_5$O$_4$ requires 295.1280).

EXAMPLE 6

2-Amino-9-[2-(2,2-dimethyl-1,3-dioxan-5-yl)ethyl]purine

To a suspension of 2-amino-9-(4-hydroxy-3-hydroxymethylbut-1-yl)purine (240 mg, 1.0 mmol) in N,N-dimethylformamide (3 ml) were added p-toluenesulphonic acid monohydrate (210 mg, 1.1 mmol) and 2,2-dimethoxypropane (0.62 ml, 5.0 mmol) and the solution was stirred for 30 minutes. Potassium carbonate (110 mg, 0.8 mmol) was added and the solution was stirred for a further 30 minutes. Water (10 ml) was added and the solution was extracted with chloroform (3×8 ml). The organic layers were combined, dried (magnesium sulphate) and the solvent removed. Trituration with toluene-ether afforded 2-amino-9-[2-(2,2-dimethyl-1,3-dioxan-5-yl)ethyl]purine as a white crystalline solid (262 mg, 94%) which was recrystallised from ethyl acetate-hexane (216 mg, 78%), m.p. 118°–120°; $\lambda_{max}$ (MeOH) 221 (27,200), 244 (4,920), and 308 (7,130)nm; $\nu_{max}$ (KBr) 3450, 3140, 1635, 1615, 1580, and 1435 cm$^{-1}$; $\delta_H$ [(CD$_3$)$_2$SO] 1.26 (3H, s, CH$_3$), 1.33 (3H, s, CH$_3$), 1.58 (1H, m, 3'-H), 1.74 (2H, q, J 7.1 Hz, 2'-H), 3.54 (2H, dd, J 11.8 Hz and 8.5 Hz, 2×H$_{ax}$), 3.78 (2H, dd, J 11.8 Hz and 4.4 Hz, 2×H$_{eq}$), 4.07 (2H, t, J 7.2 Hz, 1'-H), 6.46 (2H, s, D$_2$O exchangeable, 2-NH$_2$), 8.09 (1H, s, 8-H), and 8.56 (1H, s, 6-H); (Found: C, 56.09; H, 6.91; N, 24.88%. C$_{13}$H$_{19}$N$_5$O$_2$ requires C, 56.30; H, 6.91; N, 25.25%).

EXAMPLE 7

2-Amino-9-(4-propionyloxy-3-propionyloxymethylbut-1-yl)purine

A solution of 2-amino-9-(4-hydroxy-3-hydroxymethylbut-1-yl)purine (0.21 g, 0.9 mmol), 4-dimethylaminopyridine (10 mg) and propionic anhydride (0.64 ml, 5.0 mmol) in N,N-dimethylformamide (5 ml)

was stirred for 16 hours. The solvent was removed and the residue was partitioned between aqueous sodium bicarbonate and chloroform. The organic layer was dried (magnesium sulphate) and the solvent was removed. The residue was purified by column chromatography on silica gel eluting with chloroform-methanol (20:1) to give 2-amino-9-(4-propionyloxy-3-propionyloxymethylbut-1-yl)purine (160 mg, 51%) which was recrystallised from ethyl acetate-hexane (115 mg, 37%), m.p. 77.5°–79°; $\lambda_{max}$ (EtOH) 222 (27,300), 244 (5,020), and 309 (7,110)nm; $\delta_{max}$ (KBr) 3390, 3210, 1735, 1650, 1605, 1580, 1525, 1475, and 1425 cm$^{-1}$; $\delta_H$ (CDCl$_3$) 1.14 (6H, t, J 7.6 Hz, 2×CH$_3$), 1.96 (3H, m, 2'-H and 3'-H), 2.34 (4H, q, J 7.6 Hz, 2×CH$_2$CH$_3$), 4.15 (4H, d, J 5.5 Hz, 2×CH$_2$OOC), 4.21 (2H, t, J 7.0 Hz, 1'-H), 5.05 (2H, s, D$_2$O exchangeable, 2-NH$_2$), 7.77 (1H, s, 8-H), and 8.69 (1H, s, 6-H); (Observed M+349.1752. C$_{16}$H$_{23}$N$_5$O$_4$ requires 349.1751).

9-(3-Hydroxymethyl-4-monomethoxytrityloxybut-1-yl)-2-monomethoxytritylaminopurine (Example 8) and 9-(4-Hydroxy-3-hydroxymethylbut-1-yl)-2-monomethoxytritylaminopurine (Example 9)

To a suspension of 2-amino-9-(4-hydroxy-3-hydroxymethylbut-1-yl)purine (2.37 g, 10 mmol) in N,N-dimethylformamide (40 ml) containing 4-dimethylaminopyridine (30 mg) and triethylamine (4.2 ml) was added a solution of monomethoxytrityl chloride (6.8 g, 22 mmol) in N,N-dimethylformamide (60 ml) over a period of 40 minutes. The solution was stirred for a further 40 minutes, methanol (1 ml) was added and the solvent was removed. The residue was taken up in chloroform and washed with water and dilute aqueous sodium bicarbonate. The organic layer was dried (magnesium sulphate) and the solvent was removed. The residue was purified by column chromatography on silica gel eluting with chloroform-methanol mixtures (40:1 to 6:1).

The first product to elute was 9-(3-hydroxymethyl-4-monomethoxytrityloxybut-1-yl)-2-monomethoxytritylaminopurine which was further purified by a second silica gel column eluting with chloroform-methanol (40:1) and obtained as a colourless foam (3.34 g, 43%); $\lambda_{max}$ (EtOH) 227 (47,400) and 312 (6,450)nm; $\nu_{max}$ (KBr) 3430, 1615, 1580, 1510, 1490, and 1415 cm$^{-1}$; $\delta_H$ [(CD$_3$)$_2$SO] 1.37 (2H, m, 2'-H), 1.49 (1H, m, 3'-H), 2.8–2.9 (2H, m, CH$_2$OC), 3.2–3.4 (2H, m, CH$_2$OH), 3.64 (5H, m, 1'-H and OCH$_3$), 3.73 (3H, s, OCH$_3$), 4.40 (1H, t, J 5.0 Hz, D$_2$O exchangeable, OH), 6.7–7.4 (28H, m, Ar-H), 7.46 (1H, s, D$_2$O exchangeable, 2-NH), 7.88 (1H, s, 8-H), and 8.53 (1H, s, 6-H); (Found: C, 77.28; H, 6.27; N, 8.94%. C$_{50}$H$_{47}$N$_5$O$_4$ requires C, 76.80; H, 6.06; N, 8.96%

The second product to elute was 9-(4-hydroxy-3-hydroxymethylbut-1-yl)-2-monomethoxytritylaminopurine which was obtained as a white crystalline solid after trituration and filtration from ether (2.07 g, 41%), m.p. 181°–183°; $\nu_{max}$(EtOH) 227 (36,000) and 312 (6,780)nm; $\nu_{max}$ (KBr) 3390, 1615, 1580, 1525, 1510, 1490, and 1420 cm$^{-1}$; $\delta_H$[(CD$_3$)$_2$SO] 1.30 (1H, m, 3'-H), 1.39 (2H, q, J 6.8 Hz, 2'-H), 3.15–3.35 (4H, m, 2×4'-H), 3.70 (3H, s, OCH$_3$), 3.76 (2H, t, J 7.2 Hz, 1'-H), 4.33 (2H, t, J 5.1 Hz, D$_2$O exchangeable, 2×OH), 6.8–7.4 (14H, m, Ar-H), 7.52 (1H, s, D$_2$O exchangeable, 2-NH), 7.97 (1H, s, 8-H), and 8.52 (1H, s, 6-H); (Found: C, 70.49; H, 6.24; N, 13.41%. C$_{30}$H$_{31}$N$_5$O$_3$ requires C, 70.71; H, 6.13; N, 13.74%).

EXAMPLE 10

2-Amino-9-(4-butyryloxy-3-hydroxymethylbut-1-yl)purine

To a solution of 9-(3-hydroxymethyl-4-monomethoxytrityloxybut-1-yl)-2-monomethoxytritylaminopurine (0.70 g, 0.9 mmol) and 4-dimethylaminopyridine (10 mg) in N,N-dimethylformamide (5 ml) was added butyric anhydride (0.29 ml, 1.8 mmol) and the solution was stirred for 15 minutes. Methanol (1 ml) was added and the solvent was removed. The residue was taken up in 80% acetic acid (9 ml) and the solution was stirred at 70° for 30 minutes. Water (2 ml) was added and the solution was extracted with hexane (2×10 ml). The aqueous layer was retained and the solvent was removed. The residue was partitioned between saturated aqueous sodium bicarbonate and chloroform and the organic layer was dried (magnesium sulphate) and the solvent removed. The residue was purified by column chromatography on silica gel eluting with chloroform-methanol (16:1 to afford 2-amino-9-(4-butyryloxy-3-hydroxymethylbut-1-yl)purine which was obtained as a white crystalline solid after trituration with methanol (188 mg, 68%), m.p. 125°–127°; $\lambda_{max}$ (MeOH) 222 (27,600), 243 (4,830), and 308 (6,950)nm; $\nu_{max}$ (KBr) 3190, 1730, 1640, 1620, and 1580 cm$^{-1}$; $\delta_H$ [(CD$_3$)$_2$SO]0.85 (3H, t, J 7.4 Hz, CH$_3$), 1.50 (2H, sextet, J 7.3 Hz, CH$_2$CH$_2$CH$_3$), 1.68 (1H, m, 3'-H), 1.82 (2H, m, 2'-H), 2.23 (2H, t, J 7.4 Hz, CH$_2$CH$_2$CH$_3$), 3.42 (2H, t, J 5.2 Hz, D$_2$O exchange gives d, CH$_2$OH), 3.95–4.1 (2H, ABX, J$_{AB}$ 11.0 Hz, J$_{AX}$=J$_{BX}$ 5.8 Hz, CH$_2$OOC), 4.12 (2H, t, J 7.3 Hz, 1'-H), 4.62 (1H, t, J 4.9 Hz, D$_2$O exchangeable, OH), 6.44 (2H, s, D$_2$O exchangeable, 2-NH$_2$), 8.06 (1H, s, 8-H), and 8.56 (1H, s, 6-H); (Found: C, 54.41; H, 6.91; N, 22.70%. C$_{14}$H$_{21}$N$_5$O$_3$ requires C, 54.71; H, 6.89; N, 22.79%).

EXAMPLE 11

2-Amino-9-(4-benzoyloxy-3-hydroxymethylbut-1-yl)purine

To a solution of 9-(3-hydroxymethyl-4-monomethoxytrityloxybut-1-yl)-2-monomethoxytritylaminopurine (0.70 g, 0.9 mmol) and 4-dimethylaminopyridine (10 mg) in N,N-dimethylformamide (5 ml) was added benzoic anhydride (0.61 g, 2.7 mmol) and the solution was stirred for 1 hour. Methanol (1 ml) was added and the solvent was removed. The residue was taken up in 80% acetic acid (9 ml) and the solution was stirred at 80° for 20 minutes. Water (3 ml) was added and the solution was extracted with hexane (2×10 ml). The aqueous layer was retained and the solvent was removed. The residue was partitioned between saturated aqueous sodium bicarbonate and chloroform and the organic layer was dried (magnesium sulphate) and the solvent removed. The residue was purified by column chromatography on silica gel eluting with chloroform-methanol (14:1) to afford 2-amino-9-(4-benzoyloxy-3-hydroxymethylbut-1-yl)purine which was obtained as a white crystalline solid after trituration with methanol (235 mg, 76%), m.p. 116°–118°; $\lambda_{max}$ (MeOH) 223 (36,700) and 309 (6,680)nm; $\nu_{max}$ (KBr) 3320, 1710, 1610, and 1580 cm$^{-1}$; $\delta_H$[(CD$_3$)$_2$SO]1.83 (1H, m, 3'-H), 1.93 (2H, q, J 7.1 Hz, 2'-H), 3.52 (2H, t, J 5.3 Hz, D$_2$O exchange gives d, CH$_2$OH), 4.19 (2H, t, J 7.0 Hz, 1'-H), 4.2–4.3 (2H, ABX, J$_{AB}$ 11.0 Hz, J$_{AX}$=J$_{BX}$ 5.6 Hz, CH$_2$OOC), 4.69 (1H, t, J 5.2 Hz, D$_2$O exchangeable, OH), 6.43 (2H, s, D$_2$O exchangeable, 2-NH$_2$), 7.5–7.9

(5H, m, $C_6H_5$), 8.10 (1H, s, 8-H), and 8.55 (1H, s, 6-H); (Found: C, 59.20; H, 5.63; N, 20.82%. $C_{17}H_{19}N_5O_3$ requires C, 59.81; H, 5.61; N, 20.52%).

EXAMPLE 12

2-Amino-9-(4-hydroxy-3-hydroxymethylbut-1-yl)purine 4'-phosphate

To an ice-cooled solution of phosphorus oxychloride (0.10 ml, 1.1 mmol) in pyridine (2 ml) was added dropwise over 15 minutes a solution of 9-(3-hydroxymethyl-4-monomethoxytrityloxybut-1-yl)-2-monomethoxytritylaminopurine (0.78 g, 1.0 mmol) in pyridine (2 ml). The solution was stirred for a further 5 minutes at 0° and then for 30 minutes at room temperature. The solution was added dropwise to a solution of sodium bicarbonate (0.5 g, 6.0 mmol) in water (7 ml). The solvent was removed and the residue was taken up in 80% acetic acid (10 ml) and the solution was stirred at 70° for 25 minutes. The solvent was removed and the residue was taken up in water and brought to pH 6 by addition of ammonia. The solution was extracted twice with chloroform and the solvent was removed. The residue was purified by preparative high pressure liquid chromatography on a $C_{18}$ reverse-phase μ-Bondapack column eluting with 3% methanol in ammonium acetate buffer (pH 4.5, 50 mM) to afford 2-amino-9-(4-hydroxy-3-hydroxymethylbut-1-yl)purine 4'-phosphate as a hygroscopic white powder (85 mg, 25%); $\lambda_{max}$ ($H_2O$) 220, 241, and 303 nm; $\nu_{max}$ (KBr) 3410, 1660, 1620, and 1580 cm$^{-1}$; $\delta_H$ [$(CD_3)_2SO$] 1.57 (1H, m, 3'-H), 1.77 (2H, m, 2'-H), 3.37 (2H, d, J 4.4 Hz, $CH_2OH$), 3.77 (2H, t, J 5.6 Hz, $CH_2OP$), 4.12 (2H, t, J $\overline{7.4}$ Hz, 1'-H), 6.48 (2H. s, $D_2O$ exchangeable, 2-$NH_2$), 8.08 (1H, s, 8-H), and 8.54 (1H, s, 6-H); (Found: C, 35.53; H, 5.93; N, 22.24%. $C_{10}H_{16}N_5O_5P.0.5NH_3.H_2O$ requires C, 34.94; H, 5.72; N, 22.41%).

EXAMPLE 13

2-Amino-9-(4-hydroxy-3-hydroxymethylbut-1-yl)purine 4':4''-phosphate

To an ice-cooled solution of phosphorus oxychloride (93 μl, 1.0 mmol) in pyridine (2 ml) was added dropwise over 45 minutes a solution of 9-(4-hydroxy-3-hydroxymethylbut-1-yl)-2-monomethoxytritylaminopurine (0.46 g, 0.9 mmol) in pyridine (4 ml). The solution was stirred for a further 20 minutes at room temperature and was then added dropwise to a solution of sodium bicarbonate (0.34 g, 4.0 mmol) in water (6 ml). The solvent was removed and the residue was taken up in 80% acetic acid (9 ml) and the solution was stirred at 70° for 25 minutes. The solvent was removed and the residue was taken up in water and brought to pH 6 by addition of ammonia. The solution was extracted twice with chloroform and the solvent was removed. The residue was purified by preparative high pressure liquid chromatography on a $C_{18}$ reverse-phase μ-Bondapack column eluting with 4% methanol in ammonium acetate buffer (pH 4.5, 50 mM) to afford 2-amino-9-(4-hydroxy-3-hydroxymethylbut-1-yl) purine 4':4''-phosphate as a white powder (225 mg, 75%); $\lambda_{max}$ ($H_2O$) 220, 242, and 303 nm; $\nu_{max}$ (KBr) 2900–3200 (br), 1705, 1615, and 1580 cm$^{-1}$; $\delta_H$ [$(CD_3)_2SO$] 1.63 (1H, m, 3'-H), 1.74 (2H, q, J 7.0 Hz, 2'-H), 3.80 (2H, q, J 9.2 Hz, 2×$H_{ax}$), 3.98 (2H, ddd, J 14.3, 10.9, and 3.5 Hz, 2×$H_{eq}$), 4.08 (2H, t, J 7.1 Hz, 1'-H), 6.51 (2H, s, $D_2O$ exchangeable, 2-$NH_2$), 8.10 (1H, s, 8-H), and 8.56 (1H, s, 6-H); (Found: C, 36.41; H, 5.18; N, 22.38%. $C_{10}H_{14}N_5O_4P.0.3$ $NH_3$. $1.5H_2O$ requires C, 36.25; H, 5.45; N, 22.40%).

BIOLOGICAL DATA

Xanthine Oxidase Catalysed Oxidation of 2-Amino-9-(4-hydroxy-3-hydroxymethylbut-1-yl)purine To an aqueous solution of 2-amino-9-(4-hydroxy-3-hydroxymethylbut-1-yl)purine (0.5 mM, 0.7 ml; pH7) was added bovine milk xanthine oxidase (20 μl, 0.4 unit). Dissolved atmosphere oxygen was allowed to act as electron acceptor and changes in the UV spectrum were measured. After 4 minutes 25% conversion had occurred and after 2.5 hours conversion was essentially complete. The oxidation product was identified as 9-(4-hydroxy-3-hydroxymethylbut-1-yl)guanine by its UV spectrum and HPLC retention time.

(Incubation of 9-(4-hydroxy-3-hydroxymethylbut-1-yl)guanine with xanthine oxidase under identical conditions resulted in no change over a 2 hour period.)

Oral Absorption of 2-Amino-9-(4-hydroxy-3-hydroxymethylbut-1-yl)purine and 2-Amino-9-(4-acetoxy-3-acetoxymethylbut-1-yl)purine and their Conversion to 9-(4-hydroxy-3-hydroxymethylbut-1-yl)guanine in Mice

Procedure

2-Amino-9-(4-hydroxy-3-hydroxymethylbut-1-yl)purine, 2-amino-9-(4-acetoxy-3-acetoxymethylbut-1-yl)purine and 9-(4-hydroxy-3-hydroxymethylbut-1-yl)guanine were administered by oral gavage (0.2 mmoles/kg in 0.1 ml of 1% carboxymethyl cellulose) to 20 g female Balb/C mice which had been starved for 18 hours. Fifteen, 60 and 180 minutes later, blood was collected from three mice per time point by cardiac puncture using heparinised syringes. Equal aliquots at each time were pooled and an equal volume of 16% trichloroacetic acid added. Following centrifugation (8,500 g) to remove precipitated proteins, 0.5 ml of supernatant was immediately added to 0.1 ml of saturated sodium bicarbonate solution and the resulting mixture analysed by high performance liquid chromatography or stored at −20° C. prior to analysis.

Results

| | Administered Compound | Concentration of 9-(4-hydroxy-3-hydroxymethylbut-1-yl)guanine (μg/ml) in blood at stated times after administration | | |
|---|---|---|---|---|
| | | 15 min | 1 hr | 3 hr |
| Expt. 1 | 9-(4-Hydroxy-3-hydroxymethylbut-1-yl(guanine | 0.7 | 0.4 | 0.1 |
| | 2-Amino-9-(4-hydroxy-3-hydroxymethylbut-1-yl)purine | 3.0 | 2.2 | 0.3 |
| | 9-(4-Hydroxy-3-hydroxy- | 1.3 | 1.0 | 0.4 |

-continued

| | Administered Compound | Concentration of 9-(4-hydroxy-3-hydroxy-methylbut-1-yl)guanine (μg/ml) in blood at stated times after administration | | |
|---|---|---|---|---|
| | | 15 min | 1 hr | 3 hr |
| Expt. 2 | methylbut-1-yl)guanine 2-Amino-9-(4-hydroxy-3-hydroxymethylbut-1-yl)purine | 4.6 | 2.8 | 0.6 |
| | 2-Amino-9-(4-acetoxy-3-acetoxymethylbut-1-yl)purine | 18.7 | 4.3 | 0.3 |
| Expt. 3 | 9-(4-Hydroxy-3-hydroxymethylbut-1-yl)guanine | 1.4 | 1.1 | 0.5 |
| | 2-Amino-9-(4-hydroxy-3-hydroxymethylbut-1-yl)purine | 4.8 | 4.6 | 1.2 |
| | 9-(4-acetoxy-3-hydroxymethylbut-1-yl)-2-aminopurine | 12.9 | 5.1 | 0.3 |
| | 2-Amino-9-(3-hydroxymethyl-4-methoxycarbonyloxybut-1-yl)purine | 13.7 | 5.6 | 0.7 |
| | 2-Amino-9-[2-(2,2-dimethyl-1,3-dioxan-5-yl)ethyl]purine | 8.4 | 2.8 | 0.8 |
| Expt. 4 | 9-(4-Hydroxy-3-hydroxymethylbut-1-yl)guanine | 1.1 | 0.9 | 0.4 |
| | 2-Amino-9-(4-hydroxy-3-hydroxymethylbut-1-yl)purine | 3.5 | 4.0 | 0.8 |
| | 2-Amino-9-(4-propionyloxy-3-propionyloxymethylbut-1-yl)purine | 20.0 | 6.6 | 0.5 |
| | 2-Amino-9-(4-butyryloxy-3-hydroxymethylbut-1-yl)purine | 16.2 | 7.1 | 0.5 |
| | 2-Amino-9-(4-benzoyloxy-3-hydroxymethylbut-1-yl)purine | 16.0 | 6.6 | 0.3 |
| Expt. 5 | 9-(4-hydroxy-3-hydroxymethylbut-1-yl)guanine | 1.3 | 1.0 | 0.2 |
| | 2-amino-9-(4-hydroxy-3-hydroxymethylbut-1-yl)purine | 4.1 | 4.1 | 1.4 |
| | 2-amino-9-(4-hydroxy-3-hydroxymethylbut-1-yl)purine 4'-phosphate | 2.2 | 4.3 | 1.3 |
| | 2-amino-9-(4-hydroxy-3-hydroxymethylbut-1-yl)purine 4': 4''-phosphate | 0.2 | 0.2 | 0.7 |

We claim:

1. A compound of Formula (I)

(I)

$$R_1O-CH_2-CH(-CH_2-OR_2)-(CH_2)_2-N\text{-purine}$$

or a pharmaceutically acceptable salt thereof, where $R_1$ and $R_2$ are each independently hydrogen, or a carboxylic acyl provided that $R_1$ and $R_2$ are not both hydrogen; or $R_1$ and $R_2$ are joined together to form a cyclic cetal group or a cyclic carbonate group.

2. A compound according to claim 1 wherein $R_1$ and/or $R_2$ is a carboxylic acyl group such that the group $R_1O-$ and/or $R_2O-$ is a pharmaceutically acceptable ester group.

3. A compound according to claim 2 wherein the carboxylic acyl group $R_1$ and/or $R_2$ is a group $$R_3C(=O)-$$

wherein $R_3$ is $C_{1-6}$ alkyl, $C_{1-6}$ alkoxy or aryl optionally substituted with one or two groups selected from $C_{1-6}$ alkyl, $C_{1-6}$ alkoxy and halo.

4. A compound according to claim 1 wherein $R_1$ and $R_2$ are joined together to form a group $$\diagdown C=O,$$

or $$\diagdown C(C_{1-3}\text{alkyl})_2.$$

5. A compound according to claim 4 wherein $R_1$ and $R_2$ are joined together as a $C(CH_3)_2$ group.

6. A compound according to claim 1 selected from
2-amino-9-(4-acetoxy-3-acetoxymethylbut-1-yl)purine;
2-amino-9-(4-acetoxy-3-hydroxymethylbut-1-yl)purine;
2-amino-9-(3-hydroxymethyl-4-methoxycarbonyloxybut-1-yl)purine;
2-amino-9-[2-(2,2-dimethyl-1,3-dioxan-5-yl)ethyl]purine;
2-amino-9-(4-propionyloxy-3-propionyloxymethylbut-1-yl)purine;
2-amino-9-(4-butyryloxyl-3-hydroxymethylbut-1-yl)purine;
2-amino-9-(4-benzoyloxyl-3-hydroxymethylbut-1-yl)purine;
and pharmaceutically acceptable salts thereof.

7. A pharmaceutical composition for treating viral infections which comprises a compound of formula (I) as defined in claim 1 in combination with a pharmaceutically acceptable carrier.

8. A method of treating viral infections in a human or non-human animal, which comprises administering to the animal an effective, non-toxic amount of a compound of formula (I) or a pharmaceutically acceptable salt thereof.

9. A compound named 2-amino-9-(4-acetoxy-3-acetoxymethylbut-1-yl)purine

10. A method of treating herpesvirus infection in a human or non-human animal, which comprises administering to the animal an effective, non-toxic amount of a compound of formula (I) or a pharmaceutically acceptable salt thereof.

11. A method of claim 10 wherein the herpesvirus is herpes simplex type 1 (HSV-1).

12. A method of claim 10 wherein the herpesvirus is herpes simplex type 2 (HSV-2).

13. A method of claim 10 wherein the herpesvirus is varicella zoster.

14. A method of claim 8 wherein the compound is 2-amino-9-(4-acetoxy-3-acetoxymethylbut-1-yl)purine.

15. A method of claim 10 wherein the compound is 2-amino-9-(4-acetoxy-3-acetoxymethylbut-1-yl)purine or a pharmaceutically acceptable salt thereof.

16. A method of claim 15 wherein the herpesvirus is herpes simplex type 1 (HSV-1).

17. A method of claim 15 wherein the herpesvirus is herpes simplex type 2 (HSV-2).

18. A method of claim 15 wherein the herpesvirus is varicella zoster.

19. A pharmaceutical composition of claim 7 wherein the compound is 2-amino-9-(4-acetoxy-3-acetoxymethylbut-1-yl)purine.

* * * * *

UNITED STATES PATENT AND TRADEMARK OFFICE
CERTIFICATE OF CORRECTION

PATENT NO. : 5,246,937

DATED : Sep. 21, 1993

INVENTOR(S) : Harnden et al.

It is certified that error appears in the above-identified patent and that said Letters Patent is hereby corrected as shown below:

In the left hand column of the cover page under "Related U.S. Application Data", line 1, reads:
"Division of Ser. No. 285, 399, Dec. 6, 1991, abandoned," should read:
--Division of Ser. No. 285, 399, Dec. 15, 1988, abandoned.

Column 1, line 5, reads:
"07/285,399 filed Dec. 6, 1991 now abandoned which is", should read:
--07/285,399 filed Dec. 15, 1988 now abandoned which is--.

Column 1, line 32, reads:
"tion properties and is converted in vivo to the com-", should read:
--tion properties and is converted in vivo to the com- --.

Column 8, line 54, reads:
"$\lambda$max ($H_2O$) 242 and 303 nm; $\lambda$max (KBr) 3320, 3210", should read:
--$\lambda$max ($H_2O$) 242 and 303 nm; vmax (KBr) 3320, 3210--.

Column 10, line 25, reads:
"3'-H), 1.81 (2H, m, 2'-H), 3.41 (2H, t, 5.1 Hz, $D_2O$ ex-" should read:
--3'-H), 1.81 (2H, m, 2'-H), 3.41 (2H, t, J 5.1 Hz, $D_2O$ ex- --.

Column 10, line 37, reads:
"dimethylformamide (3 ml) were added p-toluenesul-" should read:
--dimethylformamide (3 ml) were added p-toluenesul- --.

Column 11, line 10, reads:
"244 (5,020), and 309 (7,110)nm; $\delta_{max}$ (KBr) 3390, 3210," should read:
--244 (5,020), and 309 (7,110)nm; $v_{max}$ (KBr) 3390, 3210,--.

UNITED STATES PATENT AND TRADEMARK OFFICE
CERTIFICATE OF CORRECTION

PATENT NO. : 5,246,937

DATED : Sep. 21, 1993

INVENTOR(S) : Harnden et al.

It is certified that error appears in the above-identified patent and that said Letters Patent is hereby corrected as shown below:

Column 11, line 14, reads:
"2'-H and 3'-H), 2.34 (4H, q, J 7.6 Hz, 2 X $CH_2CH_3$), 4.15" should read:
--2'-H and 3'-H), 2.34 (4H, q, J 7.6 Hz, 2 X $\underline{CH_2}CH_3$), 4.15--.

Column 11, line 59, reads:
"(2.07 g, 41%), m.p. 181°-183°; $v_{max}$ (EtOH) 227 (36,000)" should read:
--(2.07 g, 41%), m.p. 181°-183°; $\lambda_{max}$ (EtOH) 227 (36,000)--.

Signed and Sealed this

Ninth Day of August, 1994

Attest:

BRUCE LEHMAN

*Attesting Officer*       *Commissioner of Patents and Trademarks*

UNITED STATES PATENT AND TRADEMARK OFFICE
CERTIFICATE OF CORRECTION

PATENT NO.   :   5,246,937
DATED        :   Sep. 21, 1993
INVENTOR(S)  :   Harnden et al.

It is certified that error appears in the above-identified patent and that said Letters Patent is hereby corrected as shown below:

On the cover page under "ABSTRACT", the structure reads:

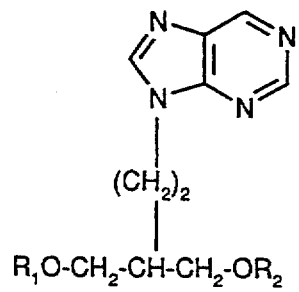

the structure should read:

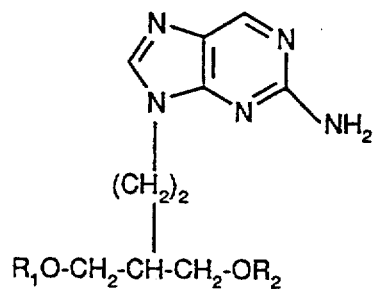

UNITED STATES PATENT AND TRADEMARK OFFICE
CERTIFICATE OF CORRECTION

PATENT NO. : 5,246,937
DATED : Sep. 21, 1993
INVENTOR(S) : Harnden et al.

It is certified that error appears in the above-identified patent and that said Letters Patent is hereby corrected as shown below:

In the claims, the structure in Claim 1 reads:

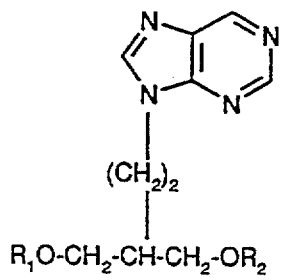

the structure should read:

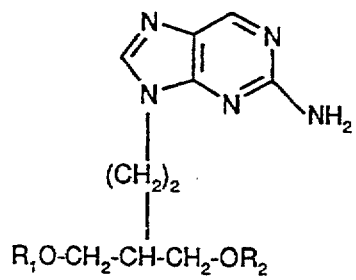

Signed and Sealed this

Twentieth Day of June, 1995

Attest:

BRUCE LEHMAN

Attesting Officer          Commissioner of Patents and Trademarks